United States Patent [19]
Brierley

[11] Patent Number: 6,128,075
[45] Date of Patent: Oct. 3, 2000

[54] DIAMOND ANVIL SPECTROSCOPE

[75] Inventor: Philip R. Brierley, Madison, Wis.

[73] Assignee: Pike Technologies of Wisconsin, Inc., Madison, Wis.

[21] Appl. No.: 09/277,533

[22] Filed: Mar. 26, 1999

Related U.S. Application Data

[63] Continuation-in-part of application No. 08/964,508, Nov. 5, 1997, Pat. No. 5,965,889.

[51] Int. Cl.[7] .............................. G01N 21/01; G01J 5/02
[52] U.S. Cl. ......................... 356/244; 356/440; 356/300; 250/341.8; 250/340; 250/341.1
[58] Field of Search .................................. 356/244, 300, 356/440; 250/341.8, 340, 341.1, 339.11, 339.12

[56] References Cited

U.S. PATENT DOCUMENTS

| | | | |
|---|---|---|---|
| 5,046,854 | 9/1991 | Weller et al. | 356/440 |
| 5,093,580 | 3/1992 | Sting | 250/571 |
| 5,172,182 | 12/1992 | Sting et al. | 356/244 |
| 5,200,609 | 4/1993 | Sting et al. | 250/226 |
| 5,210,418 | 5/1993 | Harrick et al. | 250/339 |
| 5,552,604 | 9/1996 | Sting et al. | 250/341.2 |
| 5,616,922 | 4/1997 | Reffner et al. | 250/339.12 |
| 5,703,366 | 12/1997 | Sting et al. | 250/341.2 |

OTHER PUBLICATIONS

Applicant's Exhibit A, "DuraSampllR" four–page color brochure of Applied Systems, Inc., Norwalk, CT, 1996, admitted prior art.

Applicant's Exhibit B, "Single Bounce HATR Accessory" two–page brochure of Spectra–Tech, Inc., Shelton, CT, 1996, admitted prior art.

Applicant's Exhibit C, "Thunderdome" two–page brochure of Spectra–Tech, Inc., Shelton, CT, undated, admitted prior art.

Applicant's Exhibit D, "The Split Pea Accessory", three–page brochure of Harrick Scientific, undated, admitted prior art.

Applicant's Exhibit E, "Golden Gate Single Reflection Diamond ATR", two–page brochure of Specac Ltd., undated, admitted prior art.

A dual beam total internal reflection fluorescence spectrometer for dynamic depth resolved measurements of biochemical liquid solid interface binding reactions in opaque solvents. L.W. Liebmann, J.A. Robinson and K.G. Mann; Rev. Sc. Instrum. 62(9), Sep. 1991, pp. 2083–2092.

Micro–optic system for reflectance measurements at pressures to 70 kilobar. B. Welber, Rev. Sci. Instrum. 48(4), Apr. 1977, pp. 395–395.

Microoptic double beam system for reflectance and absorption measurements at high pressure. K. Syassen, R. Sonnenschein, Rev. Sci. Instrum. 53(5), May 1982, pp. 644–650.

Internal Reflectance Spectroscopy by N. J. Harrick, pp. 89–145.

*Primary Examiner*—Frank G. Font
*Assistant Examiner*—Roy M. Punnoose
*Attorney, Agent, or Firm*—Quarles & Brady LLP

[57] ABSTRACT

A stage for an infrared spectroscope has a focusing body and a sampling element spaced apart by a mounting fixture. The focusing body and sampling element optically cooperate by transmission and internal refraction and reflection to focus an infrared beam on a sample surface and to collect the beam for analysis after it was reflected from the sample surface. The sampling element is made of a durable material and can be removably mounted in the fixture.

19 Claims, 5 Drawing Sheets

DIAMOND ANVIL SPECTROSCOPE

CROSS-REFERENCE TO RELATED APPLICATIONS

The present invention is a continuation-in-part of patent application Ser. No. 08/964,508 filed on Nov. 5, 1997, now U.S. Pat. No. 5,965,889.

STATEMENT REGARDING FEDERALLY SPONSORED RESEARCH OR DEVELOPMENT

BACKGROUND OF THE INVENTION

The present invention relates to Fourier transform infrared spectrometer's (FTIR spectrometers) and, in particular, to a stage for use with such a spectrometer for making attenuated total reflectance (ATR) measurements.

Fourier transform infrared spectroscopy is a technique for studying the composition of matter by measuring the characteristic absorption of specific wavelengths of infrared radiation. The sample may be measured either with transmitted or reflected radiation.

In transmission spectroscopy, a beam of infrared radiation of known and time variant spectral composition is passed through a transmissive sample. The resulting transmission absorption spectrum is then compared to standard transmission absorption spectra to identify spectral absorption characteristics of the sample permitting identification of the sample's constituents.

With opaque samples, the technique of specular reflection spectroscopy may be used. In reflection spectroscopy, the beam of infrared radiation is directed against the surface of a sample at a predetermined angle of incidence. The spectrum of the energy reflected at an opposing reflection angle is then measured. As with transmission spectroscopy, the resulting reflection absorption spectrum may be compared to known reflection absorption spectra to reveal information about the composition of the sample or the coating of the surface of the sample. One type of specular reflection measurement is termed attenuated total reflectance (ATR) spectroscopy.

Making ATR measurements of a material involves placing the material against the sample surface of an infrared transmitting crystal, often referred to as internal reflection elements (IREs). Infrared light is introduced into the IRE crystal and made to internally reflect off the sample surface. During this reflection, the sample may absorb some of the energy of the infrared beam which interacts with the sample. A successful measurement requires that the sample be in intimate contact with the IRE since this interaction with the infrared beam only occurs over a few microns from its surface.

IREs that allow for a single internal reflection are called single-bounce IREs. Single-bounce IREs may come in a variety of shapes including trapezoidal shape prisms, cylindrical rods or hemispherical domes. They offer the advantages of requiring only a small sample and of needing only low clamping forces to hold the sample against the sample surface. The drawback to single-bounce IREs is that there is only one interaction between the sample and crystal and the resulting spectrum may be weak.

In order to increase the light energy coupled to the sample, multi-bounce IREs may be used. In multi-bounce IREs, multiple reflections occur against the side of the crystal contacting the sample to increase the amount of attenuation and improve the obtained spectra. Multi-bounce crystals require that the sample be held in close proximity to the crystal over a relatively broad area which increases the total force that must be applied to the sample.

Single and multi-bounce crystals are typically limited to having a single transmissive element so as to reduce Fresnel reflection losses occurring when light passes into or out of a transmissive element. One problem with both types of crystals is that not all the light passing through the IRE strikes the sample surface. The light that does not strike the sample surface is commonly termed stray light and may distort the spectral features that are being investigated.

Additionally, solid samples must be pressed against the IRE, especially in multi-bounce systems. If a solid sample is rough or abrasive it may damage the sample surface of the IRE. Minute nicks and scratches in the sample surface of the IRE can cause optical anomalies which degrade the performance of the spectroscope.

Hard materials with the proper spectral characteristics, such as diamonds, can provide a suitable scratch-resistant surface on which to place a solid sample. The size and cost of diamonds, however, effectively prohibits diamonds from being made into focusing lenses. And, cost notwithstanding, its hardness makes it difficult to machine the convex and/or concave surfaces needed for a lens.

SUMMARY OF THE INVENTION

The present invention provides a stage for an infrared spectroscope with two separate transmissive elements. The first transmissive element is a single or multiple bounce sampling element upon which a sample may be placed. The sampling element is made of a hard, scratch-resistant material, such as diamond, having the necessary spectral properties for internal reflection. The second transmissive element is a focusing body of the proper size and shape to focus an image of an infrared source on a sample surface of the sampling element and re-focus the image of reflected light on a spectrometer detector.

In particular, the present invention provides a stage for an infrared spectrometer that has a source of infrared radiation and a radiation detector. A focusing body has opposed front and rear surfaces that converge at edges, the rear surface defining a focal surface at its center. A sampling element has an entrance face, an exit face and a sample surface against which a sample may be placed. A first portion of the front surface refracts a beam of infrared radiation from the radiation source through the first portion of the front surface into the focusing body so as to direct the beam to a first portion of the rear surface. The first portion of the rear surface reflects the beam through the focusing body to a second portion of the front surface. The second portion of the front surface reflects the beam through the focusing body to a first portion of the focal surface which transmits the beam to the entrance face of the sampling element. The entrance face refracts the beam through the sampling element to the sample surface which reflects the beam through the sampling element to the exit face which in turn transmits the beam to a second portion of the focal surface of the focusing body. The second portion of the focal surface refracts the beam through the focusing body to a third portion of the front surface which reflects the beam through the focusing body to a second portion of the rear surface. The second portion of the rear surface reflects the beam through the focusing body to a fourth portion of the front surface, which transmits the beam to the radiation detector.

The present invention overcomes the problems of spectral distortion between two IRE elements and provides a stage for a spectroscope having two transmissive elements one of which is a single bounce sampling element.

The sampling element may also have a bottom surface joined to the sample surface by the entrance and exit faces. The bottom surface internally reflect the infrared beam at least one time from a first portion to a second portion of the sample surface. The beam is then directed to a final portion of the sample surface which internally reflects the beam to the exit face. The beam is transmitted from the exit face to the second portion of the focal surface in the focusing body.

Thus, the present invention also provides for a spectroscope stage with a multi-bounce sampling element. The multi-bounce sampling element provides increased beam attenuation and enhanced spectra reception, which improve the accuracy of the measurements of the spectroscope.

Preferably, the sample element is made of diamond. Because the focusing and sampling elements are separate pieces, the sampling element can be made small enough so that it is not cost-prohibitive. Diamond is the hardest known substance and provides the stage with a highly scratch resistant sampling surface, which is particularly important for a multi-bounce sampling element.

Additionally, the transmissive elements must be held by a fixture so that an air gap exists between the focusing body and the sampling element. The air gap prevents the elements from contacting each other in the event the fixture flexes from the clamping force holding a hard solid sample in intimate contact with the sample surface. The air gap thus prevents abrasion or wear between the elements as well as deflection or a change in shape of the focusing body. This provides the further advantage of a spectroscope that is not readily susceptible to wear nor degradation of its beam focusing capability.

The fixture may be monolithic or in two sections, and the sampling element may be mounted in various configurations. The two-piece fixture of the present invention, allows the sampling element to be removed, cleaned and replaced if necessary.

DETAILED DESCRIPTION OF THE PREFERRED EMBODIMENTS

Figure 1:
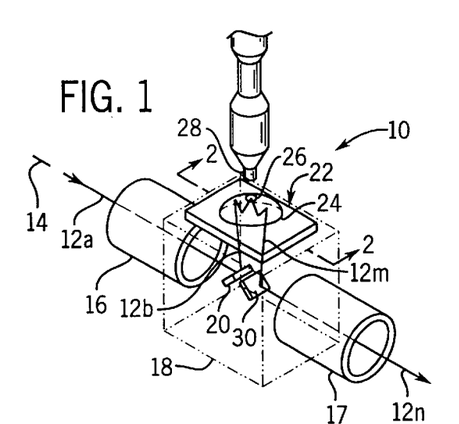
FIG. 1 is a perspective view of a spectrometer stage of the present invention showing the optical path from the spectrometer source through the IRE elements and back to the spectrometer detector.

Referring to FIG. 1, a stage 10 for an FTIR spectrometer is positioned to receive an infrared beam 12a modulated according to well-known FTIR techniques. The beam 12a is received along a principal axis 14 through a first tubular shroud 16 to the body 18 of the stage 10.

A front surface mirror 20 canted at 45° with respect to axis 14 reflects infrared beam 12a upward as infrared beams 12b toward an IRE assembly 22 holding a generally disk shaped focusing body 23 and a much smaller, preferably conical, sampling element 24. Because the elements 23,24 are separate and the sampling element 24 is small, the sampling element 24 can be made of a scratch-resistant, but more expensive, material without significantly increasing the cost of the spectroscope.

The focusing body 23 receives the infrared beams 12b and, as will be described, focuses it on a sample surface 26 being a generally horizontal circular area. The sample surface 26 is positioned beneath a micrometer anvil 28 such as may be used to compress a sample (not shown) downward against the sample surface 26 in the case of solid samples. Light reflected internally off the sample surface 26 is returned into the body 18 of the stage 10 as downward traveling infrared beams 12m. There it is directed, by a second front surface mirror 30 angled at 45° with respect to axis 14, as horizontally traveling infrared beam 12n through second tubular shroud 17 generally aligned with axis 14 and infrared beam 12a.

Figure 2:
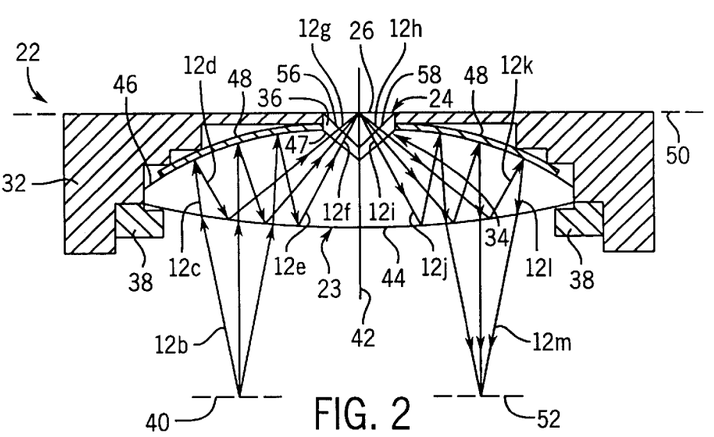
FIG. 2 is a side cross-section taken along line 2—2 of FIG. 1 showing the invention having single bounce IRE elements consisting of a focusing body and a sampling element spaced apart by a one-piece mounting fixture.

Referring now to FIGS. 2, the IRE assembly 22 includes a metallic stage fixture 32 having a generally horizontal planer upper surface with a central aperture in which the sampling element 24 may be suspended above a focal surface 34 at the center of the focusing body 23. The sampling element 24, with the sample surface 26 at its upper surface, is positioned so that an air gap 36 exists between it and the focal surface 34 in the focusing body 23. The air gap 36 prevents any deflection of the fixture 32 from causing the sampling element 24 from contacting, and possibly damaging, the focusing body 23. The fixture 32 may be threaded about its periphery (not shown) for mating with a retaining ring (not shown) that may hold a well adapter (not shown) against the upper surface of the fixture 32. The well adapter may have a central conical aperture aligned with the sample surface 26 to hold liquid samples. The focusing body 23 is held at its periphery and is sealed within the IRE assembly 22 by a metallic gasket. The gasket seals small gaps, accommodates thermal expansion and provides support for the focusing body 23. The focusing body 23 is held within a cavity against the gasket by means of a retaining ring 38.

Figure 3:
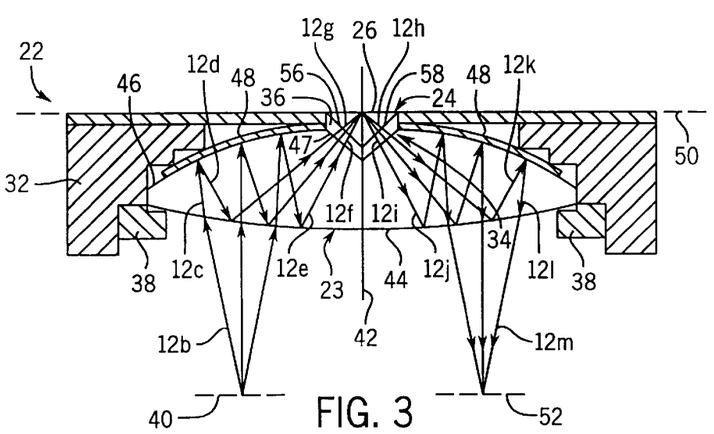
FIG. 3 is a side cross-section taken along line 2—2 of FIG. 1 showing the first embodiment as in FIG. 2 with the focusing body and sampling element spaced apart by a two-piece mounting fixture.

The fixture may be a one-piece, monolithic structure, as in FIG. 2, or a two-piece structure as in FIG. 3 with the upper planar surface being detachable. A monolithic fixture 32 is used when the sampling element 24 is made of hard material, such as diamond, that is not readily susceptible to surface scratches and has would not need to be refurbished or replaced. A two-piece structure is used with a sampling element 24 made from a less rugged material, so that if damaged, it could be replaced easily.

FIGS. 2–3 illustrate the IRE assembly 22 with a single bounce sampling element 24 and the focusing body 23 having a depression 47 at the focal surface 34. In general, the focusing body 23 will receive light from an infrared source at image plane 40 positioned beneath a left side of the focusing body 23. This light is focused again at the sample surface 26 and reflected light from the sample surface 26 is focused again at image plane 52 positioned beneath a right side of the focusing body 23. The image at image plane 52 will be refocussed as an image on the infrared detector (not shown).

The focusing body 23 is radially symmetric about an axis 42 perpendicular to axis 14. The focusing body 23 has a convex front surface 44 and a convex rear surface 46 which defines the depression 47 at its center along axis 42. In a first embodiment, the depression 47 is an inverted conical shape having a surface that is of the size and shape necessary to receive the sampling element 24, which is also conical in a first embodiment.

Beams 12b passing from each point in image plane 40 are received over a first area of the front surface 44 and refracted to form beams 12c passing through the focusing body 23 and directed toward the rear surface 46. The material of the focusing body 23 is transparent to infrared radiation and conducts the beams 12c to a first portion of the rear surface 46 to the left of the depression 47. The rear surface 46 may be coated with a thin layer of aluminum 48 to aid in completely reflecting the rays.

The rear surface 46 other than the depression 47 is generally convex so as to reflect infrared beams 12c as beams 12d in focused fashion toward the front surface 44 at an angle of incidence sufficient to provide for complete internal reflection of beams 12d (as beams 12e) by a second portion of the front surface 44 to the left of axis 42.

The beams 12e are internally reflected to a first portion of the depression surface 47 to the left of the axis 42 at an angle of incidence approximately equal to, but not greater than, the critical angle so that the beams 12f are transmitted across the gap 36 without significant spectral loss to an entrance face 56 of the sampling element to the left of axis 42. The curvature of the surfaces through which beams 12b pass, beams 12c, 12d and 12e are reflected, and beams 12f are transmitted are such as to bring the beams 12 (represented as 12g) into focus again at a sample image plane 50 aligned with the sample surface 26 of the sampling element 24. Thus, the focusing body 23 presents a large entrance aperture to beams 12b from image plane 40 and focuses substantially all the energy from image plane 40 on sample surface 26 of the sampling element 23.

Sampling surface 26 is normal to axis 42 and beams 12g are at a sufficient angle so as to reflect internally off of sample surface 26 as beams 12h. Sampling surface 26 is not coated with aluminum.

The reflected beams 12h are symmetric with respect to beams 12g, and in striking an exit face 58 of the sampling element to the right of the axis 42, the beams are transmitted through the gap 36 (as beams 12i) to a second portion of the depression surface 47 to the right of the axis 42. Beams 12j are internally refracted from the depression surface 47 to a third portion of the front surface 44 and internally reflected as beams 12k in much the same manner as beams 12d are reflected as beams 12e, however, the third portion of the front surface 44 is to the right of the axis 42.

Beams 12k pass through the material of the focusing body 23 to strike a second portion of the rear surface 46 to the right of the axis 42. This second portion is also coated with aluminum 48 so that beams 12k are fully reflected downward again as beams 12l to a fourth portion of the front surface 44 to the right of axis 42 where they pass out of the focusing body 23 and are transmitted as beams 12m.

The curvature of the front surface 44 and rear surface 46 are such as to cause beams 12m to form an image at image plane 52 corresponding to the images at the image planes 50 and 40.

By providing the appropriate curvatures of the surfaces 44, 46, and 47 the IRE assembly 22 may be imaging, that is may bring about a focusing of the beams at planes 40, 50 and 52 thus maximizing the amount of energy interacting with the sample (not shown) and minimizing the amount of light transmitted through the sampling element 24 that does not interact with the sample.

Figures 4A, 4B, 4C:
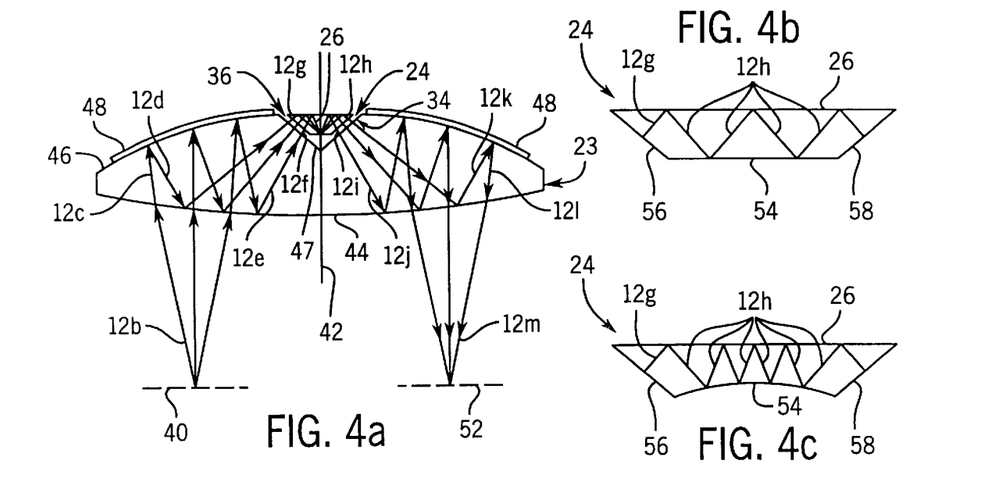
FIG. 4a is a side view of the invention having multi-bounce IRE elements consisting of a focusing body and a sampling element.
FIG. 4b is a side view of the multi-bounce sampling element of FIG. 4a, having a flat bottom surface.
FIG. 4c is a side view of the multi-bounce sampling element of FIG. 4a, having a concave bottom surface.

In an alternative, multi-bounce embodiment of the invention shown in FIGS. 4a–4c, the sampling element 24 has a bottom surface 54 opposite the sampling surface 26. In this embodiment, the beams 12f are transmitted from the first portion of the depression surface 47 of the focusing body 23 to the entrance face 56 of the sampling element 24 to the left of the axis 42. The beams 12g are refracted into focus again at the sample image plane 50 aligned with the sample surface 26 of the sampling element 24. The beams 12g contact the sample surface 26 at such an angle to internally reflect from the sample surface 26 to the bottom surface 54 as beams 12h. The beams 12h internally reflect between the sampling surface 26 and the bottom surface 54 one or more times until the beams are reflected to the exit face 58 of the sampling element 24 to the right of the axis 42 at an angle less than the critical angle. The beams 12i are transmitted across the gap to the second portion of the depression surface 47 of the focusing body 23, through the body and to the image plane 52 as described in the single bounce embodiment above.

The number of internal reflections, which determines the sampled area, depends upon the configuration of the sampling element 24 and in particular the distance between the sampling surface 26 and the bottom surface 54. As the thickness of the element is decreased, the number of bounces of the beams 12h increases. The bottom surface 54 can be flat as in FIG. 4b or have a curved or concave cross-section as in FIG. 4c. In particular, the curved bottom surface 54 of FIG. 4c may be spherical or cylindrical which maximizes the surface area of the entrance 56 and exit 58 faces of the sampling element 24 as well as the number of internal reflections or bounces of the beams 12h. With a curved bottom surface 54, the angle of incidence of the beams 12h varies along the sampling surface 26.

The focusing body 23 is preferably constructed of an optically transparent material such as zinc selenide (ZnSe) germanium or amorphous transmitting infrared glass (AMTIR), the latter being a special glass commercially available from Amorphous Materials of Garland, Tex. The sampling element 24 is also made of an optically transparent material, however, preferably it is made from an extreme hard, scratch-resistant material, such as diamond.

Other materials which may be used for either the focusing body 23 or sampling element 24 include, but are not limited to, arsenic modified selenium glass (SeAs), cadmium sulphide (Cds), cadmium telluride (CdTe), cesium iodide (CsI), diamond (C), germanium (Ge), indium antimonide (InSb), silicon (Si), sapphire (A1203), silver bromide (AgBr), silver chloride (AgCl), sulfur (S), sulphur selenium glasses (SxSey), thallium bromide (TlBr), thallium chloride (TlCl), KRS5 ((TlBr-TlCl), zinc sulphide (ZnS) and zirconia (ZrO2, cubic).

A variety of shapes of the surfaces 44 and 46 may be used, as shown and described in co-pending application Ser. No. 08/964,508, filed Nov. 5, 1997 and assigned to the assignee of this application. The disclosure of the co-pending application is hereby incorporated by reference as though fully set forth herein. Generally, surfaces 44 and 46 will be converging and in the preferred embodiment are spherical ellipsoidal surfaces. The exact surfaces may be determined for a given material and application through the use of commercially available ray tracing programs as will be understood to those of ordinary skill in the art.

Figure 5A:
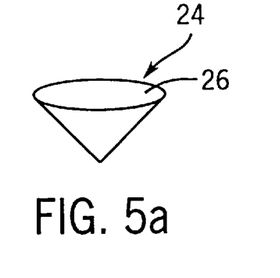
FIGS. 5a–5e show examples of various configurations of the sample element.
Figure 5B:
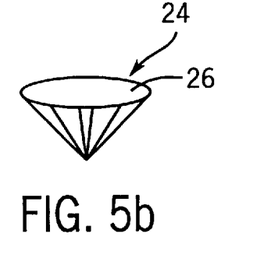
Figure 5C:
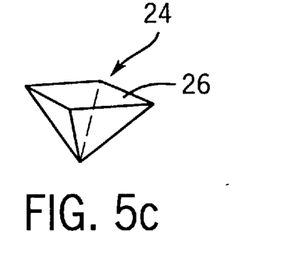
Figure 5D:
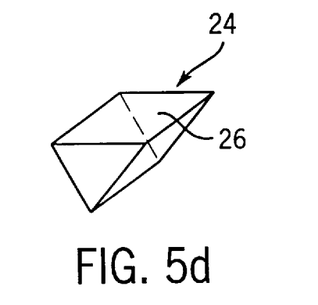
Figure 5E:
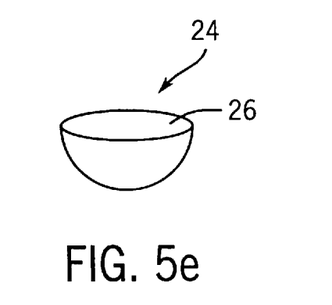
Figure 6A:
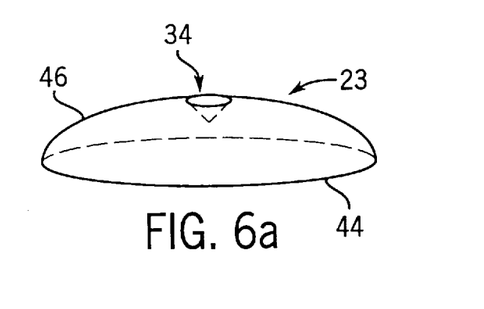
FIGS. 6a–6d show examples of various configurations of the focal surface in the focusing body corresponding to the sample element configurations of FIGS. 5a–5e.
Figure 6B:
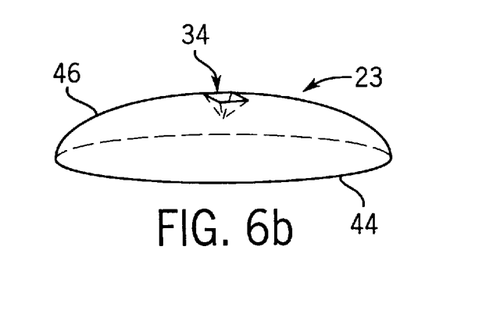
Figure 6C:
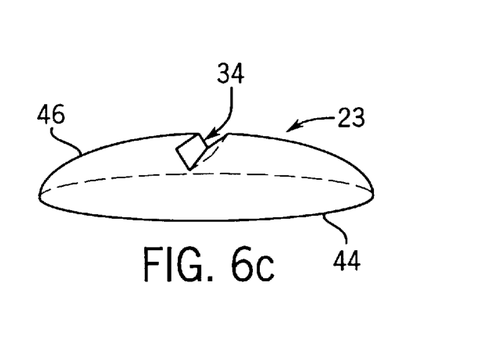
Figure 6D:
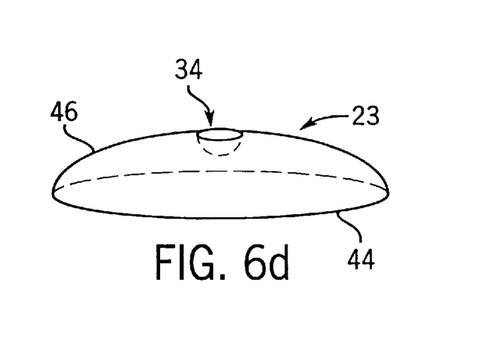

The sampling element 24 can be of various shapes, as shown in FIGS. 5*a*–5*e*. The sampling element is preferably conical, as in FIG. 5*a*, but may also take the shape of a faceted cone (FIG. 5*b*), a five-sided polyhedron having a square base (pyramid, FIG. 5*c*) or a rectangular base (prism, FIG. 5*d*), or a hemisphere (FIG. 5*e*). Similarly, as shown in FIGS. 6*a*–6*d*, the depression 47 in the focusing body 23 can be made to correspond to the various configurations of the sampling elements 24 described above. Thus, for instance, a conical or faceted sampling element 24 would be used with a focusing body 23 having a cone-shaped depression 47, as in FIG. 6*a*. And, a hemispherical sampling element 24 would be used with a hemispherical depression 47 as in FIG. 6*d*.

It is preferred that the depression 47 correspond to the configuration of the sampling element 24, however, it may be impractical or cost-prohibitive to do so for each configuration. For example, a spectroscope with a polyhedral sampling element 24 having a square base (FIG. 5*c*) would perform best with a focusing body having a pyramidal depression as in FIG. 6*b*. It may be too expensive to manufacture such a depression, however, in which case a focusing body with a less expensive V-shaped groove, as in FIG. 6*c*, could be used. Additionally, a V-shaped depression 47 can be used with both pyramid-shaped and prism-shaped sampling elements, which provides another cost advantage to this spectroscope.

The various configurations of the sampling element 24 and the focusing body depression 47 apply to both the single bounce and multi-bounce embodiments of the invention.

Figure 7:
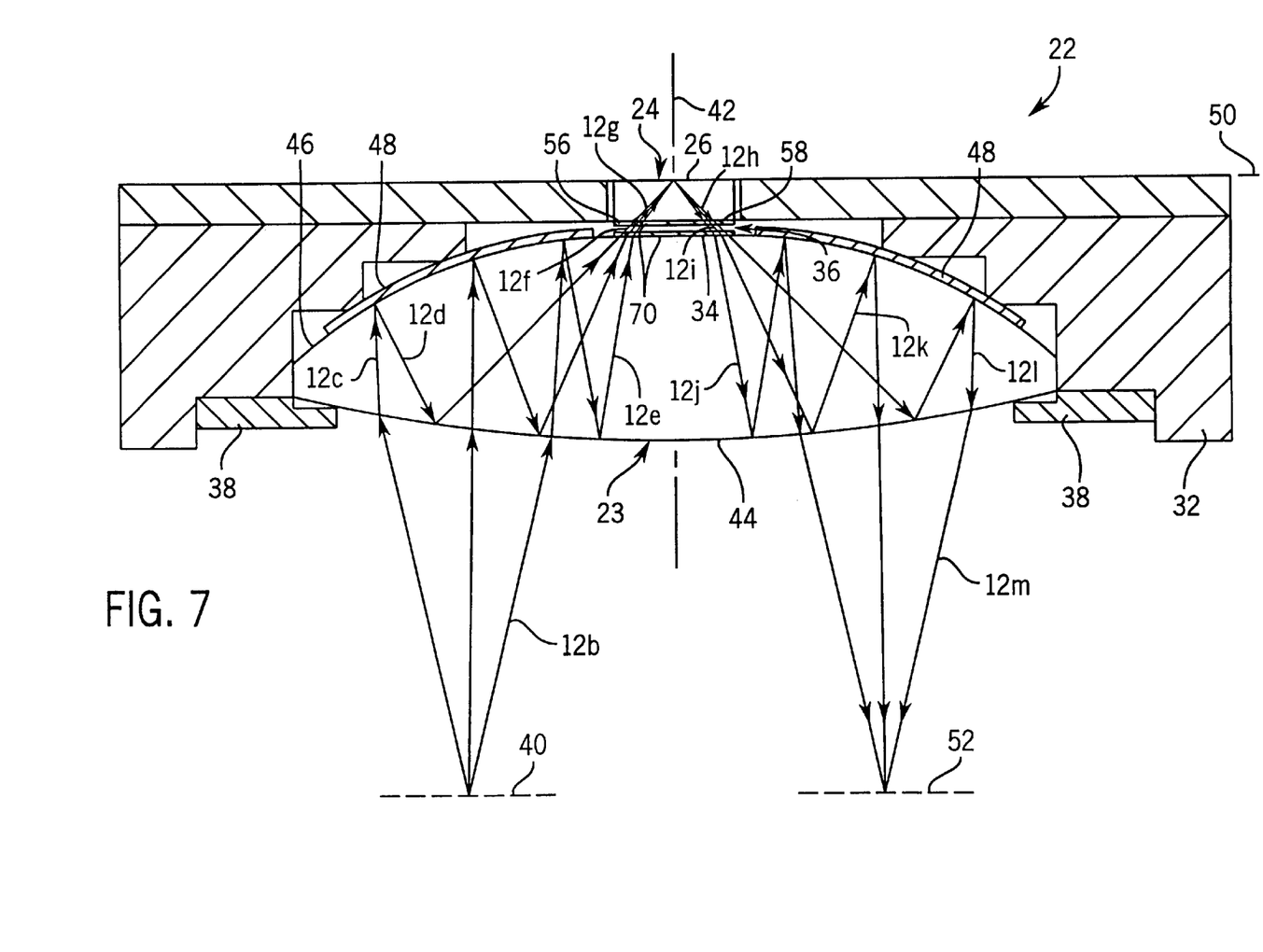
FIG. 7 is a side cross-section taken along line 2—2 of FIG. 1 showing an alternate embodiment of the invention with a single bounce sampling element.
Figure 8:
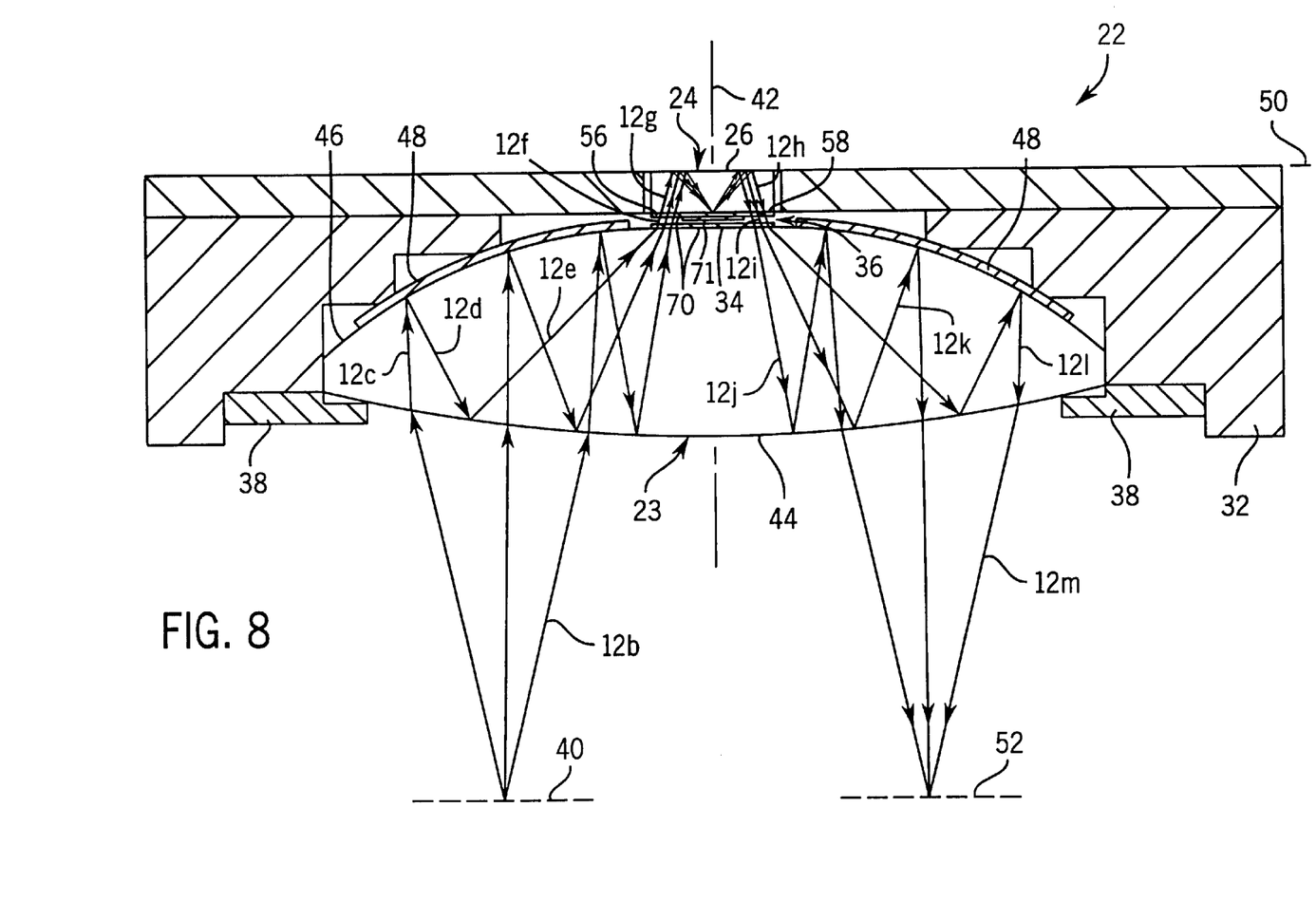
FIG. 8 is a side cross-section taken along line 2—2 of FIG. 1 showing the alternate embodiment of FIG. 7 with a multiple bounce sampling element.

Referring to FIGS. 7 and 8, in an alternate embodiment of the present invention where the sampling element has a flat or cupped surface opposing the sampling surface 54, the focal surface 34 of the focusing body may be flat. The focal surface 34 and the bottom surface 54 in this embodiment is coated with an anti-reflective film 70, which facilitates transmission of the beams 12*f* across the gap 36.

The beams 12*f* are transmitted from the first portion of the flat focal surface 34 to the entrance face 56 of the sampling element 24 to the left of the axis 42. The beams 12*g* are refracted into focus again at the sample image plane 50 aligned with the sample surface 26 of the sampling element 24. The beams 12*g* contact the sample surface 26 at such an angle to internally reflect from the sample surface 26 to the bottom surface 54 as beams 12*h*. In a multi-bounce system as shown in FIG. 8, a central portion of the bottom surface 54 is coated with a reflective film 71. The beams 12*h* internally reflect between the sampling surface 26 and the central portion of the bottom surface 54 one or more times until the beams are reflected to the exit face 58 of the sampling element 24 to the right of the axis 42 at an angle less than the critical angle. In a single bounce system, the beams 12*h* reflect off the sample surface 26 and directly exit through the exit face 58 of the sampling element 24. The beams 12*i* are transmitted across the gap to the second portion of the focal surface 34 of the focusing body 23, through the body and to the image plane 52 as described in the single bounce embodiment above.

FIGS. 9*a*–9*g* illustrate various mounting configurations of the sampling element in the fixture 32. The sampling elements 24 shown therein are diagrammatic and the mounting configurations are intended to apply to all of the above sampling element configurations for both single and multiple bounce systems. Also, in all cases the interface between the sampling element 24 and the fixture 32 may be in the form of a metallic, ceramic, plastic or compliant gasket, or an active metal braze, weld, frit seal, adhesive or one of the many forms of metallic, ceramic, glass, plastic or elastomer bonding technique.

Figure 9A:
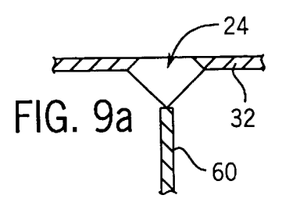
FIGS. 9a–9g show diagrammatic representations of the sample element in various mounting configurations.
Figure 9B:
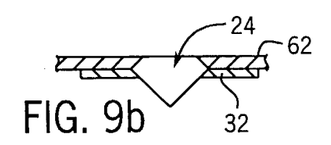
Figure 9C:
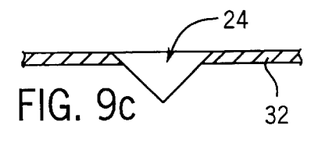
Figure 9D:
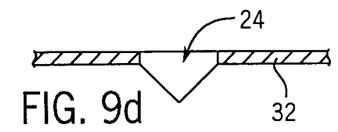
Figure 9E:
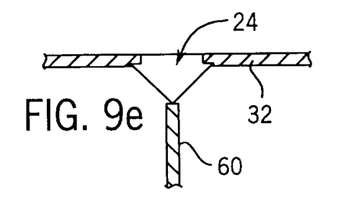
Figure 9F:
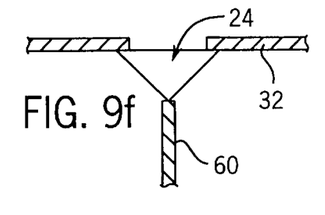
Figure 9G:
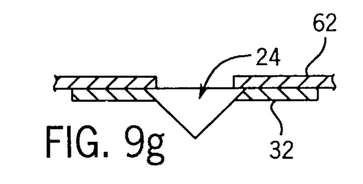

The sampling element 24 may be pressed (FIG. 9*a*), under-mounted (FIG. 9*f*) or lapped at a circumferential shoulder (FIG. 9*e*) to the planar upper surface of the fixture 32 and held in place from below by a post 60 that passes through an aperture (not shown) in the center of the focusing body 23. Alternatively, the sampling element 24 may be clamped in place so that it is flush with the clamp surface 62 (FIG. 9*b*) or the top of the upper surface (FIG. 9*g*). Finally, the sampling element may also be adhered (FIG. 9*c*) or brazed or welded (FIG. 9*d*) along its circumference to the upper surface of the fixture 32. The configurations shown in FIGS. 9*f*–9*g* provide a well for testing liquid samples so that a separate well adapter would not be needed.

The above description has been that of preferred embodiments of the present invention. It will occur to those that practice the art that many modifications may be made without departing from the spirit and scope of the invention. In order to apprise the public of the various embodiments that may fall within the scope of the invention, the following claims are made.

I claim:

1. A stage for an infrared spectrometer having a radiation source and a radiation detector, the stage comprising:

a focusing body having opposed front and rear surfaces that converge at edges, the front surface defining a focal surface at its center;

a sampling element having an entrance face, an exit face and a sample surface against which a sample may be placed wherein:

(i) a first portion of the front surface is shaped to refract a beam of infrared radiation from the radiation source through the first portion of the front surface into the focusing body so as to direct the beam to a first portion of the rear surface;

(ii) the first portion of the rear surface is shaped to internally reflect the beam through the focusing body to a second portion of the front surface;

(iii) the second portion of the front surface is shaped to internally reflect the beam through the focusing body to a first portion of the focal surface shaped to transmit the beam to the entrance face of the sampling element;

(iv) the entrance face is shaped to refract the beam through the sampling element to the sample surface which is shaped to internally reflect the beam through the sampling element to the exit face which in turn is shaped to transmit the beam to a second portion of the focal surface in the focusing body;

(v) the second portion of the focal surface is shaped to refract the beam through the focusing body to a third portion of the front surface which is shaped to internally reflect the beam through the focusing body to a second portion of the rear surface;

(vi) the second portion of the rear surface is shaped to internally reflect the beam through the focusing body to a fourth portion of the front surface, which is shaped to transmit the beam to the radiation detector.

2. The stage as recited in claim 1 wherein one of the front surface of the focusing body and the first and second portions of the rear surface of the focusing body are flat.

3. The stage as recited in claim 1 wherein the sampling element is diamond.

4. The stage as recited in claim 1 wherein the sampling element has a bottom surface opposed to the sampling surface between the entrance and exit faces, wherein:

(iv) the bottom surface is shaped to internally reflect the beam at least once from a first portion of the sample surface to a second portion of the sample surface, the second portion shaped to transmit the beam to the second portion of the focal structure in the focusing body.

5. The stage as recited in claim 4 wherein the bottom surface of the sampling element is concave.

6. The stage as recited in claim 4 wherein one of the front surface of the focusing body and the first and second portions of the rear surface of the focusing body are flat.

7. The stage as recited in claim 4 wherein the focal surface of the focusing element is flat and the focal surface and the bottom surface of the sampling element are coated with an anti-reflective film.

8. The stage as recited in claim 7 wherein a central portion of the bottom surface of the sampling element is coated with a reflective film.

9. The stage as recited in claims 1, 2 or 4 wherein the first and second portions of the rear surface of the focusing body are coated with a reflecting material.

10. The stage as recited in claims 1, 2 or 4 wherein sampling element is conical with the sample surface being the circular base of the cone, and the focal surface in the focusing body is a conical depression sized to receive the sampling element.

11. The stage as recited in claims 1, 2 or 4 wherein the sampling element is a faceted cone with the sample surface being the base of the cone, and the focal surface in the focusing body is a conical depression sized to receive the sampling element.

12. The stage as recited in claims 1, 2 or 4 wherein the sampling element is a five-sided polyhedron with the sample surface being the base of the polyhedron, and the focal surface in the focusing body is a polyhedral depression sized to receive the sampling element.

13. The stage as recited in claims 1, 2 or 4 wherein the sampling element is a triangular prism with the sample surface being one side of the prism, and the focal surface in the focusing body is a V-shaped groove sized to receive the sampling element.

14. The stage as recited in claims 1, 2 or 4 wherein the sampling element is hemispherical and the sample surface is the circular base of the hemisphere, and the focal surface in the focusing body is a hemispherical depression sized to receive the sampling element.

15. The stage as recited in claim 1 further comprising a fixture for holding the sampling element above the focal surface in the focusing body so as to be separated by an air gap.

16. The stage as recited in claim 15 wherein the fixture is monolithic.

17. The stage as recited in claim 15 wherein the fixture has at least two separable sections so that the sampling element may be removed.

18. The stage as recited in claim 15, wherein the focusing body includes a central aperture in which is disposed a post to support the sampling element from below the sample surface and bias the sampling element in contact with the fixture.

19. The stage as recited in claim 15, further comprising a clamp for mounting the sampling element to the fixture from above the sampling element.

* * * * *

UNITED STATES PATENT AND TRADEMARK OFFICE
CERTIFICATE OF CORRECTION

Patent No.   : 6,128,075
Dated        : October 3, 2000
Inventor(s)  : Philip R. Brierley It is certified that error appears in the above-identified patent and that said Letters Patent is hereby corrected as shown below:

In line 56 of column 3, delete the second occurrence of [is];
In line 64 of column 4, delete [has].

IN THE CLAIMS:

In line 8 of claim 4, replace [structure] with surface.

Signed and Sealed this

Eighth Day of May, 2001

Attest:

NICHOLAS P. GODICI

Attesting Officer   Acting Director of the United States Patent and Trademark Office